US012319641B2

(12) United States Patent
Yim et al.

(10) Patent No.: US 12,319,641 B2
(45) Date of Patent: Jun. 3, 2025

(54) LOBARIC ACID DERIVATIVE HAVING PTP-1B INHIBITORY ACTIVITY, PREPARATION METHOD THEREFOR AND USE THEREOF

(71) Applicant: SNBIOSCIENCE INC., Seoul (KR)

(72) Inventors: Joung Han Yim, Gyeonggi-do (KR); Il Chan Kim, Gyeonggi-do (KR); Se Jong Han, Gyeonggi-do (KR); Tai Kyoung Kim, Incheon (KR); Dong Gyu Jo, Gyeonggi-do (KR); Hyun Cheol Oh, Jeollabuk-do (KR); Ha Ju Park, Gyeonggi-do (KR); Seul Ki Min, Incheon (KR); Sung Jin Kim, Incheon (KR); Pil Sung Kang, Incheon (KR); Min Ju Kim, Incheon (KR); Jung Eun Kim, Incheon (KR); Kyung Hee Kim, Incheon (KR); Ju Mi Hong, Incheon (KR)

(73) Assignee: SNBIOSCIENCE INC., Seoul (KR)

( * ) Notice: Subject to any disclaimer, the term of this patent is extended or adjusted under 35 U.S.C. 154(b) by 710 days.

(21) Appl. No.: 17/637,439

(22) PCT Filed: Aug. 14, 2020

(86) PCT No.: PCT/KR2020/095109
§ 371 (c)(1),
(2) Date: Feb. 22, 2022

(87) PCT Pub. No.: WO2021/034173
PCT Pub. Date: Feb. 25, 2021

(65) Prior Publication Data
US 2022/0281805 A1  Sep. 8, 2022

(30) Foreign Application Priority Data
Aug. 22, 2019 (KR) .................. 10-2019-0103206

(51) Int. Cl.
C07C 235/84 (2006.01)
A61P 3/10 (2006.01)
C07D 321/10 (2006.01)

(52) U.S. Cl.
CPC .............. *C07C 235/84* (2013.01); *A61P 3/10* (2018.01); *C07D 321/10* (2013.01)

(58) Field of Classification Search
CPC ........ C07C 235/84; A61P 3/10; C07D 321/10
See application file for complete search history.

(56) References Cited

U.S. PATENT DOCUMENTS

2004/0214870 A1   10/2004   Xin et al.

FOREIGN PATENT DOCUMENTS

| EP | 1 496 052 A1 | 1/2005 |
|---|---|---|
| KR | 10-2010-0021489 A | 2/2010 |
| KR | 10-2012-0121274 A | 11/2012 |
| KR | 10-1481140 B1 | 1/2015 |
| KR | 10-1485162 B1 | 1/2015 |

OTHER PUBLICATIONS

Carpentier, C., et al. Bioorganic & Medicinal Chemistry 26.22 (2018): 5845-5851. (Year: 2018).*
International Search Report for PCT/KR2020/095109 mailed on Dec. 2, 2020.
Notice of Allowance issued on May 25, 2021 from Korean Patent Office in a counterpart Korean Patent Application No. 10-2019-0103206 (all the cited references are listed in this IDS.) (English translation is also submitted herewith.).
Carpentier Claudia et al., "Lobaric acid and pseudodepsidones inhibit NF-κB signaling pathway by activation of PPAR-γ", Bioorganic & Medicinal Chemistry, vol. 26, pp. 5845-5851, 2018.

* cited by examiner

*Primary Examiner* — Joseph K McKane
*Assistant Examiner* — Quincy McKoy
(74) *Attorney, Agent, or Firm* — The PL Law Group, PLLC (57) ABSTRACT

A lobamide compound according to an embodiment of the present disclosure is represented by Formula 1. The lobamide compound has excellent PTP-1B inhibitory activity that is far higher than that of conventional lobaric acid derivatives and which can be orally administered, and thus is very effective in the prevention or treatment of diabetes or obesity through oral administration.

15 Claims, 7 Drawing Sheets

LOBARIC ACID DERIVATIVE HAVING PTP-1B INHIBITORY ACTIVITY, PREPARATION METHOD THEREFOR AND USE THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2020/095109, filed Aug. 14, 2020, which claims priority to the benefit of Korean Patent Application No. 10-2019-0103206 filed in the Korean Intellectual Property Office on Aug. 22, 2019, the entire contents of which are incorporated herein by reference.

BACKGROUND

1. Technical Field

The present invention relates to a novel lobaric acid derivative having protein tyrosine phosphatase-1B (PTP-1B) inhibitory activity, preparation method therefor, and use thereof, and in particular, to a novel lobaric acid derivative that exhibits excellent performance of inhibiting PTP-1B activity as compared to the existing lobaric acid derivative, lobarstin, can be administered orally and thus is effective in preventing or treating diabetes, as well as preparation method therefor and use thereof.

2. Background Art

Diabetes mellitus is a syndrome of metabolic disorders including hyperglycemia caused by defects in insulin action, insulin secretion or both thereof. Diabetes is a disease with high potential for vascular complications in the future and can be generally divided into type 1 diabetes and type 2 diabetes. Type 1 (insulin-dependent) diabetes is caused by the destruction of beta cells in pancreatic islets by immunity and the resulting absolute lack of insulin. In the case of type 2 (non-insulin-dependent) diabetes, insulin is secreted but not in sufficient amount or, when the body does not effectively use the insulin secreted by the body, the above disease may occur. In the state of "insulin resistance" wherein cells of the body do not work effectively, the energy source in the body, especially sugar, is not desirably used, the necessary energy is insufficient and the unused sugar is accumulated in the blood more than an amount required in the blood, whereby the sugar is eventually excreted in the urine. It is one of the chronic degenerative diseases that cannot be cured fundamentally.

Characteristics of diabetes in Korea are that type 2 diabetes accounts for 99% or more and the incidence of type 1 diabetes is 1% or less. These are different from those reported in other countries aboard wherein type 2 diabetes accounts for about 80% and the incidence of type 1 diabetes is about 10%. Causes of diabetes are complex of different factors, and important factors include, for example, heredity (about 20% of family history), environment, age (about 60% between 40 to 49 years old), obesity, decreased body resistance, drug abuse and stimulation due to stress. Although the pathogenesis of diabetes has not yet been elucidated in detail, it is a disease that occurs due to polygenic causes, except for some special diabetes (e.g., MODY, etc.), and has restriction in finding consistently related genes. In other words, various genes are intricately related to the onset of diabetes, and a large number of new genes are still being discovered.

Since diabetes is caused by a variety of pathogeneses, treatment methods thereof are inevitably varied. Moreover, there are many cases where only the existing palliative treatment methods do not attain satisfactory results, therefore, a new treatment method is required. With regard to diabetes treatment research, technologies focusing on treatment of type 2 diabetes, which accounts for 90% or more of diabetic patients, are actively developing.

Research on the etiology of diabetes till now has been continued for the past 10 years, under presumption that the cause of insulin resistance is a problem with insulin receptors. At present, the research direction is transferred toward the signaling system of insulin. As a result of examining the activity of PTP-1B in adipocytes of people with obese type and non-obese type 2 diabetes, protein expression was increased by 3 times and 5.5 times, respectively, compared to the normal group. Further, it was reported that the activity appears as 71% and 88%, respectively. Furthermore, recent experimental results have been reported to demonstrate an increase in sensitivity to insulin and resistance to a high-fat diet in mice with knockout of protein tyrosine phosphatase-1B (PTP-1B). In addition, according to a number of recently published studies, it seems that substances inhibiting PTP-1B activity may overcome insulin resistance by increasing insulin sensitivity in target cells. In order to develop PTP-1B activity inhibitors from tens of thousands of compounds that have yet to be developed as drugs, the Korea Compound Bank is now conducting random mass screening in domestic area.

Meanwhile, leptin is released from adipocytes into blood, passes through the blood brain membrane and acts on receptors in the central nervous system, thereby suppressing food intake, reducing body weight and promoting energy consumption. Since a new discovery that PTP-1B regulates leptin activity itself is disclosed, it is expected that PTP-1B will induce synergistic effects when used together with a leptin agonist (Koren, S., Best Pract. Res. Clin. Endocrinol. Metab., 21:621, 2007).

Therefore, importance of inhibitors for PTP-1B is increasing in development of therapeutics for obesity and obesity-type diabetes, and there is recently a report on a leading material discovered through high throughput screening (HTS). To date, there have been no clinically successful studies on PTP-1B and development of its inhibitors, but it is known that many research groups and companies are interested in the same and the studies are continuously proceeding.

However, most inhibitors of PTP-1B had difficulties in selectivity and bioavailability because they were developed as non-hydrolyzable phosphotyrosine mimetics targeting the active site of positively charged PTP-1B (Liu, S. et al., J. Am. Chem. Soc., 130:17075, 2008).

Lichens are known to produce unique secondary metabolites different from higher plants (Ingolfsdottir, K., Phytochemistry, 61:729, 2002), and the secondary metabolites produced by these lichens mostly belong to depside, depsidone and dibenzfurane, and these compounds are thought to be associated with low growth rates of lichens (Kumar, K C S et al., J. Nat. Prod., 62:817, 1999; Huneck, S., Naturwissenschaften, 86:559, 1999). Further, different biological activities of lichen metabolites including antibiotic, antimycobacterial, antiviral, analgesic and antipyretic activities, or the like were confirmed by a screening process (Ingolfsdottir, K., Phytochemistry, 61:729, 2002; Kumar, K C S et al., J. Nat. Prod., 62:817, 1999). Therefore, interest in drug development using metabolites of lichens is gradually increasing.

It has recently been reported that metabolites extracted from Antarctic lichen have various biological actions such as antibiotic, antimycobacterial, antiviral, anti-inflammatory, anti-allergic, antipyretic, anti-proliferative and cytotoxic effects (Oksanen I, Appl Microbiol Biotechnol 2006; 73:723-34). Further, the above product is widely used in the fields of natural cosmetics and pharmaceuticals, and it is known to involve few side effects as compared to industrial products. However, there is still no adequate information regarding health-improving properties of bioactive substances in lichens and similar species with pharmaceutically potential.

In 2009, the Polar Research Institute had extracted 7 phenolic lichen metabolites from the lichen *Stereocaulon alpinum*, identified the structure thereof, and confirmed that these metabolites selectively act only on PTP-1B among the protein tyrosine dephosphorylation enzyme family, and when administered to a disease model animal, antidiabetic effects are expressed, and further confirmed that lobaric acid as a major product has $IC_{50}$ value of 0.87 µM. Among seven metabolites, lobarin, lobarstin and sodium lobarate are disclosed in Korean Patent Registration No. 10-1481140, Korean Patent Registration No. 10-1481141 and Korean Patent Registration No. 10-1485162. It is now demanded to develop an antidiabetic drug using the above compounds.

Accordingly, the present inventors have made diligent efforts to synthesize a novel derivative exhibiting stronger PTP-1B inhibitory activity than lobaric acid and derivatives thereof such as lobarin and lobarstin, which is an effective therapeutic agent for treatment of diabetes and obesity. As a result, dimethyl lobamide was synthesized by reacting lobaric acid with dimethylamine, which exhibits a very high PTP-1B inhibitory activity with $IC_{50}$=2.16 nM level, and has relatively higher polarity compared to previously reported lobaric acid and derivatives thereof, thereby making it very advantageous for formulation. Accordingly, the present invention has been completed on the basis of the finding as described above.

SUMMARY

An object of the present invention is to provide dimethyl lobamide, which is a novel compound synthesized from lobaric acid that exhibits stronger PTP-1B inhibitory activity than lobaric acid and derivatives thereof, that is, lobarin and lobarstin, as well as a pharmaceutical composition and functional food for prevention or treatment of diabetes or obesity, each of which includes the above compound as an active ingredient.

To achieve the above object, according to an aspect of the present invention, there is provided a lobamide compound represented by Formula 1 below:

[Formula 1]

in Formula 1, $R_1$ is each independently H, a C1-C10 alkyl group or a C2-C10 allyl group; $R_2$ is H, a C1-C10 alkyl group, a C2-C10 allyl group, an acyl group, a C1-C10 hydroxyalkyl group or a C1-C10 aminoalkyl group; $R_3$ is a carboxylic acid or an amide group; $R_4$ is a C1-C10 alkoxy group or a hydroxyl group; $R_5$ is a C1-C10 alkoxy or a hydroxyl group; $R_6$ is a C1-C10 alkoxy group or a hydroxyl group; and $R_7$ is an amide group.

In addition, according to another aspect of the present invention, there is provided a method for preparation of a lobamide compound represented by Formula 1, including: (a) reacting a compound having a depsidone structure represented by Formula 4 with an amine-based reagent; and (b) obtaining a compound in a form of an amide represented by Formula 1:

[Formula 1]

in Formula 1, $R_1$ is each independently H, a C1-C10 alkyl group or a C2-C10 allyl group; $R_2$ is H, a C1-C10 alkyl group, a C2-C10 allyl group, an acyl group, a C1-C10 hydroxyalkyl group or a C1-C10 aminoalkyl group; $R_3$ is a carboxylic acid or an amide group; $R_4$ is a C1-C10 alkoxy group or a hydroxyl group; $R_5$ is a C1-C10 alkoxy or a hydroxyl group; $R_6$ is a C1-C10 alkoxy group or a hydroxyl group; and $R_7$ is an amide group,

[Formula 4]

in Formula 4, $R_1$ is each independently H, a C1-C10 alkyl group or a C2-C10 allyl group; $R_2$ is H, a C1-C10 alkyl group, a C2-C10 allyl group, an acyl group, a C1-C10 hydroxyalkyl group or a C1-C10 aminoalkyl group; $R_3$ is a carboxylic acid or an amide group; $R_4$ is a C1-C10 alkoxy or a hydroxyl group; and $R_5$ is a C1-C10 alkoxy or a hydroxyl group.

Further, according to another aspect of the present invention, there is provided a method for preparation of a dimethyl lobamide compound represented by Formula 2, including: (a) reacting lobaric acid represented by Formula 3 with dimethylamine; and (b) obtaining dimethyl lobamide represented by Formula 2:

[Formula 2]

[Formula 3]

Further, according to another aspect of the present invention, there is provided a pharmaceutical composition for prevention or treatment of diabetes, comprising the lobamide compound represented by Formula 1 or a salt thereof as an active ingredient.

Furthermore, according to another aspect of the present invention, there is provided a health functional food for preventing or improving diabetes, comprising the lobamide compound represented by Formula 1 or a salt thereof as an active ingredient.

A novel compound of the present invention is synthesized from lobaric acid, which exhibits very high level ($IC_{50}$=2.16 nM) of PTP-1B inhibitory activity as compared to previously reported lobaric acid and derivatives thereof, has a relatively higher polarity to achieve very advantageous effects on formulation, thereby being used as a very effective formulation for treatment of diabetes, and can be synthesized by very simple and economical methods.

DETAILED DESCRIPTION

Unless defined otherwise, all technical and scientific terms used herein have the same meaning as commonly understood by one of ordinary skill in the art to which the present disclosure pertains. In general, the nomenclature used herein is those well-known and commonly used in the art.

In the present invention, it was confirmed that dimethyl lobamide, which is a synthetic derivative of lobaric acid isolated from the extract of *Stereocaulon alpinum*, has excellent protein tyrosine phosphatase-1B (PTP-1B) inhibitory ability compared to lobarstin, and a compound including the same can be administered orally and thus is effective in preventing or treating diabetes.

Accordingly, in one aspect, the present invention relates to a lobamide compound represented by Formula 1.

[Formula 1]

In Formula 1, $R_1$ is each independently H, a C1-C10 alkyl group or a C2-C10 allyl group; $R_2$ is H, a C1-C10 alkyl group, a C2-C10 allyl group, an acyl group, a C1-C10 hydroxyalkyl group or a C1-C10 aminoalkyl group; $R_3$ is a carboxylic acid or an amide group; $R_4$ is a C1-C10 alkoxy group or a hydroxyl group; $R_5$ is a C1-C10 alkoxy or a hydroxyl group; $R_6$ is a C1-C10 alkoxy group or a hydroxyl group; and $R_7$ is an amide group.

In addition, in another aspect, the present invention relates to a method for preparation of a lobamide compound represented by Formula 1, which includes: (a) reacting a compound having a depsidone structure represented by Formula 4 with an amine-based reagent; and (b) obtaining a compound in a form of an amide represented by Formula 1.

[Formula 1]

In Formula 1, $R_1$ is each independently H, a C1-C10 alkyl group or a C2-C10 allyl group; $R_2$ is H, a C1-C10 alkyl group, a C2-C10 allyl group, an acyl group, a C1-C10 hydroxyalkyl group or a C1-C10 aminoalkyl group; $R_3$ is a carboxylic acid or an amide group; $R_4$ is a C1-C10 alkoxy group or a hydroxyl group; $R_5$ is a C1-C10 alkoxy or a hydroxyl group; $R_6$ is a C1-C10 alkoxy group or a hydroxyl group; and $R_7$ is an amide group.

[Formula 4]

In Formula 4, $R_1$ is each independently H, a C1-C10 alkyl group or a C2-C10 allyl group; $R_2$ is H, a C1-C10 alkyl group, a C2-C10 allyl group, an acyl group, a C1-C10 hydroxyalkyl group or a C1-C10 aminoalkyl group; $R_3$ is a carboxylic acid or an amide group; $R_4$ is a C1-C10 alkoxy or a hydroxyl group; and $R_5$ is a C1-C10 alkoxy or a hydroxyl group.

Further, in another aspect, the present invention relates to a method for preparation of a dimethyl lobamide compound represented by Formula 2, which includes: (a) reacting lobaric acid represented by Formula 3 with dimethylamine; and (b) obtaining dimethyl lobamide represented by Formula 2.

[Formula 2]

[Formula 3]

Further, in another aspect, the present invention relates to a pharmaceutical composition for prevention or treatment of diabetes containing the lobamide compound represented by Formula 1, dimethyl lobamide represented by Formula 2, or salts thereof, respectively, as an active ingredient. Further, dimethyl lobamide according to the present invention may be provided as a functional food containing the same as an active ingredient. Accordingly, in another aspect, the present invention relates to a functional food for preventing or improving diabetes, including the lobamide compound represented by Formula 1, dimethyl lobamide represented by Formula 2, or salts thereof, respectively, as an active ingredient.

Hereinafter, the present invention will be described in detail.

In the present invention, after isolating lobaric acid from an extract of *Stereocaulon alpinum*, a novel compound lobaric acid represented by Formula 2 is synthesized from the isolated lobaric acid and then named dimethyl lobamide.

In one embodiment of the present invention, the lichen *Stereocaulon alpinum* (Hedw.) (GL Sm.) was collected from the Barton Peninsular located around the Sejong Base (S62° 13.3', W58° 47.0') on King George Island, Antarctica in January 2017, and then used. Lobaric acid was extracted from dried *Stereocaulon alpinum* with ethyl acetate for 4 hours and mixed with 1 N HCl solution, followed by stirring the same for 12 hours to obtain crystals. The extract was loaded on a flash column chromatography (5×25 cm) filled with silica gel (C18), and 50%, 60%, 70%, 80%, 90% and 100% (v/v) methanol (MeOH) were sequentially injected, followed by isolation of lobaric acid of Formula 3.

[Formula 3]

Thereafter, the obtained lobaric acid was dissolved in DMSO and dimethylamine was added thereto, followed by reaction under stirring the mixture. Then, 1N HCl could be added to the above reacted product while stirring, thus to obtain dimethyl lobamide by crystallization. The obtained dimethyl lobarine could be dissolved in EtOH after filtration and recrystallized by adding 0.5 N HCl to obtain crystals, followed by filtration, thus to produce dimethyl lobamide of Formula 2 below.

[Formula 2]

The lobaric acid is preferably extracted from *Stereocaulon alpinum*.

The method of the present invention may include: recrystallizing the *Stereocaulon alpinum* extract to obtain crystals containing lobaric acid; dissolving the crystals in a solvent and adding dimethylamine under stirring; and adding an acidic solution thereto so as to terminate the reaction.

There has been reported neither on PTP-1B inhibitory activity of the dimethyl lobamide, nor on medical efficacy to treat diabetes and obesity.

In one embodiment of the present invention, as a result of comparative analysis for the inhibitory activity of dimethyl lobamide on PTP-1b with lobaric acid, $IC_{50}$ of lobaric acid was 870 nM, whereas dimethyl lobamide had $IC_{50}$=2.16 nM, demonstrating excellent PTP-1b inhibitory effects, therefore, it was confirmed that dimethyl lobamide is a substance useable for pharmacological treatment and prevention of diabetes.

Moreover, in one embodiment of the present invention, as an in vitro level experiment to examine the efficacy of dimethyl lobamide, expression change of the proteins involved in the glucose uptake mechanism of HepG2 (liver cancer cells) was analyzed.

The pharmaceutical composition for prevention or treatment of diabetes, which includes the lobamide compound represented by Formula 1, dimethyl lobamide represented by Formula 2, salts thereof, respectively, as an active ingredient according to the present invention may further include an antidiabetic compound. Such antidiabetic compound may be selected from the group consisting of nateglinide, repaglinide, glitazones, sulfonyl urea, metformin, glimepride, thiazolidinedione, biguanide, acarbose as alpha-glucosidase inhibitor, and meglitinide-based frandins.

In the present invention, lobamide of Formula 1 or dimethyl lobamide of Formula 2 may be in the form of a pharmaceutically acceptable salt. The pharmaceutically acceptable salt in the present invention may be prepared by any conventional method in the art, and may form a salt with an inorganic acid such as hydrochloric acid, hydrogen bromide, sulfuric acid, sodium hydrogen sulfate, phosphoric acid, carbonic acid, etc. or a salt of pharmaceutically acceptable acid with an organic acid such as formic acid, acetic acid, oxalic acid, benzoic acid, citric acid, tartaric acid, gluconic acid, gestisic acid, fumaric acid, lactobionic acid, salicylic acid, or acetylsalicylic acid (aspirin) etc., or may react with an alkali metal ion such as sodium or potassium, etc. to form a metal salt thereof, or with an ammonium ion to form another type of pharmaceutically acceptable salt.

The pharmaceutical composition including the compound according to the present invention may be formulated and used in the form of oral dosage forms such as powders, granules, tablets, capsules, suspensions, emulsions, syrups, aerosols, etc., external preparations, suppositories, and sterile injection solutions, respectively, according to conventional methods. Carriers, excipients and diluents possibly included in the composition containing the compound may include, for example, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate and mineral oil.

In the case of formulation, it may be prepared using diluents or excipients, such as commonly used fillers, extenders, binders, wetting agents, disintegrants, and surfactants. Solid preparations for oral administration may include tablets, pills, powders, granules, capsules, etc., and these solid preparations may be prepared by admixing at least one excipient, for example, starch, calcium carbonate, sucrose or lactose, gelatin, etc. with the above compound. In addition to simple excipients, lubricants such as magnesium stearate and talc may also be used. Liquid formulations for oral administration may include suspensions, solutions, emulsions, syrups, etc. In addition to water and liquid paraffin, which are commonly used simple diluents, various excipients such as wetting agents, sweeteners, fragrances, preservatives, etc. may be included.

Formulations for parenteral administration may include sterile aqueous solutions, non-aqueous solutions, suspensions, emulsions, lyophilized formulations, and suppositories. Non-aqueous solvents and suspensions may include propylene glycol, polyethylene glycol, vegetable oils such as olive oil, and injectable esters such as ethyl oleate. As a base of the suppository, witepsol, macrogol, tween 60, cacao butter, laurin, glycerogelatin, and the like may be used.

The functional food of the present invention may include, for example, various foods, candy, chocolate, beverage, gum, tea, vitamin complex, health supplement, and the like, and may be used in the form of powder, granule, tablet, capsule or beverage.

The compound of the present invention may be added to food or beverage for the purpose of preventing diabetes and obesity. At this time, an amount of sodium lobarate in food or beverage may generally range from 0.01 to 50% by weight ("wt. %"), preferably 0.1 to 20 wt. % of a total food weight in the health functional food composition of the present invention, and with regard to the health drink composition, the compound of the present invention may be added in a ratio of 0.02 to 10 g, and preferably 0.3 to 1 g based on 100 ml of the composition.

The health beverage composition of the present invention is not particularly limited in terms of liquid components except that the compound of the present invention is contained as an essential component in the indicated ratio, and may contain various flavoring agents or natural carbohydrates as additional components like a conventional beverage. Examples of the natural carbohydrate include monosaccharides such as glucose, fructose, etc., disaccharides such as maltose, sucrose, etc., polysaccharides, for example, typical sugars such as dextrin, cyclodextrin, etc., and sugar alcohols such as xylitol, sorbitol, erythritol, etc. As flavoring agents, natural flavoring agents (thaumatin, stevia extract (e.g., rebaudioside A, glycyrrhizin, etc.)) and synthetic flavoring agents (saccharin, aspartame, etc.) may be advantageously used. A proportion of the natural carbohydrate generally ranges from about 1 to 20 g, and preferably about 5 to 12 g per 100 ml of the composition of the present invention. In addition to the above components, the functional food of the present invention may also contain various nutrients, vitamins, minerals (electrolytes), flavoring agents such as synthetic and natural flavoring agents, coloring agents and thickeners (cheese, chocolate, etc.), pectic acid and a salt thereof, alginic acid and a salt thereof, organic acids, protective colloidal thickeners, pH adjusters, stabilizers, preservatives, glycerin, alcohols, carbonation agents used in carbonated beverages and the like. Further, the functional food of the present invention may also contain natural fruit juice and pulp for production of fruit juice beverages and vegetable beverages. These components may be used independently or in combination. The proportion of these additives is not critical, but is generally selected in the range of 0 to about 20 parts by weight ("wt. parts") per 100 wt. parts of the composition of the present invention.

Further, in another aspect, the present invention relates to the use of lobamide represented by Formula 1 or dimethyl lobamide represented by Formula 2, which are synthesized from a compound isolated from the *Stereocaulon alpinum* extract, for prevention or treatment of diabetes or obesity, or the use of dimethyl lobamide synthesized from lobaric acid for prevention or treatment of diabetes or obesity.

In the present invention, dimethyl lobamide synthesized from the compound isolated from the *Stereocaulon alpinum* extract shows excellent inhibitory effects on PTP-1B activity. Therefore, in another aspect, the present invention provides a method for inhibiting PTP-1B activity using lobamide represented by Formula 1 or dimethyl lobamide represented by Formula 2, which were synthesized from a compound isolated from the *Stereocaulon alpinum* extract, or a method for inhibiting PTP-1B activity using dimethyl lobamide synthesized from lobaric acid.

Furthermore, in another aspect, the present invention relates to a composition for inhibiting PTP-1B activity, which includes dimethyl lobamide synthesized from a compound isolated from the *Stereocaulon alpinum* extract, or a composition for inhibiting PTP-1B activity, which includes dimethyl lobamide synthesized from lobaric acid.

In one embodiment of the present invention, as a result of observing the change in body weight by oral administration of dimethyl lobamide, the body weight reducing effects were demonstrated, and thus, it was confirmed that dimethyl lobamide is a substance enabling pharmacological treatment and prevention of obesity.

Accordingly, in another aspect, the present invention relates to a pharmaceutical composition for prevention or treatment of obesity, which includes the lobamide compound represented by Formula 1, dimethyl lobamide represented by Formula 2, or salts thereof, respectively, as an active ingredient. Further, dimethyl lobamide according to the present invention may be provided in a functional food containing the same as an active ingredient. Accordingly, in another aspect, the present invention provides a functional food for preventing or improving obesity, which includes the lobamide compound represented by Formula 1, dimethyl lobamide represented by Formula 2, or salts thereof, respectively, as an active ingredient.

Hereinafter, the present invention will be described in more detail through examples. These examples are only for illustrating the present invention, and it will be apparent to those skilled in the art that the scope of the present invention is not limited to these examples.

EXAMPLE

Example 1: Synthesis of Dimethyl Lobamide

Example 1-1: Preparation of Lobaric Acid from Lichen *Stereocaulon alpinum* Extract Lichen *Stereocaulon alpinum* was collected from the Barton Peninsular near the Sejong Base (S62° 13.3', W58° 47.0') on King George Island, Antarctica, in January 2017, which is lichen easily collected from the Barton Peninsular. After pulverizing 50 g of the dried *Stereocaulon alpinum* in a mixer, the mixture was extracted twice with 2 L of ethyl acetate and stirred with 1N HCl for 12 hours to obtain 5.5 g of the extract. The obtained extract was loaded on a flash column chromatography (5×25 cm) filled with silica gel (C18), followed by forming a stepwise concentration gradient with 50%, 60%, 70%, 80%, 90% and 100% (v/v) methanol (MeOH), thereby obtaining each fraction. Lobaric acid of Formula 3 was isolated at a concentration of 90% (330 mg)

[Formula 3]

Example 1-2: Synthesis of Dimethyl Lobamide 100 mg (0.22 mmol) of lobaric acid obtained in Example 1-1 was dissolved in 20 mL of DMSO, and then cooled to 0° C. Then, 6 mL of 20% dimethylamine was slowly added to the lobaric acid solution. After stirring for 30 minutes while maintaining at 0° C., the reaction was continued for 1 hour after raising the temperature to room temperature. 200 mL of 1N HCl was introduced to terminate the reaction, followed by stirring the mixture at room temperature for 12 hours to produce crystals. The resulting crystals were filtered to obtain dimethyl lobamide of Formula 2.

[Scheme 1]

Lobaric acid

Dimethyl lobamide

[Formula 2]

Example 2: Structural Analysis of Dimethyl Lobamide

Figure 1:
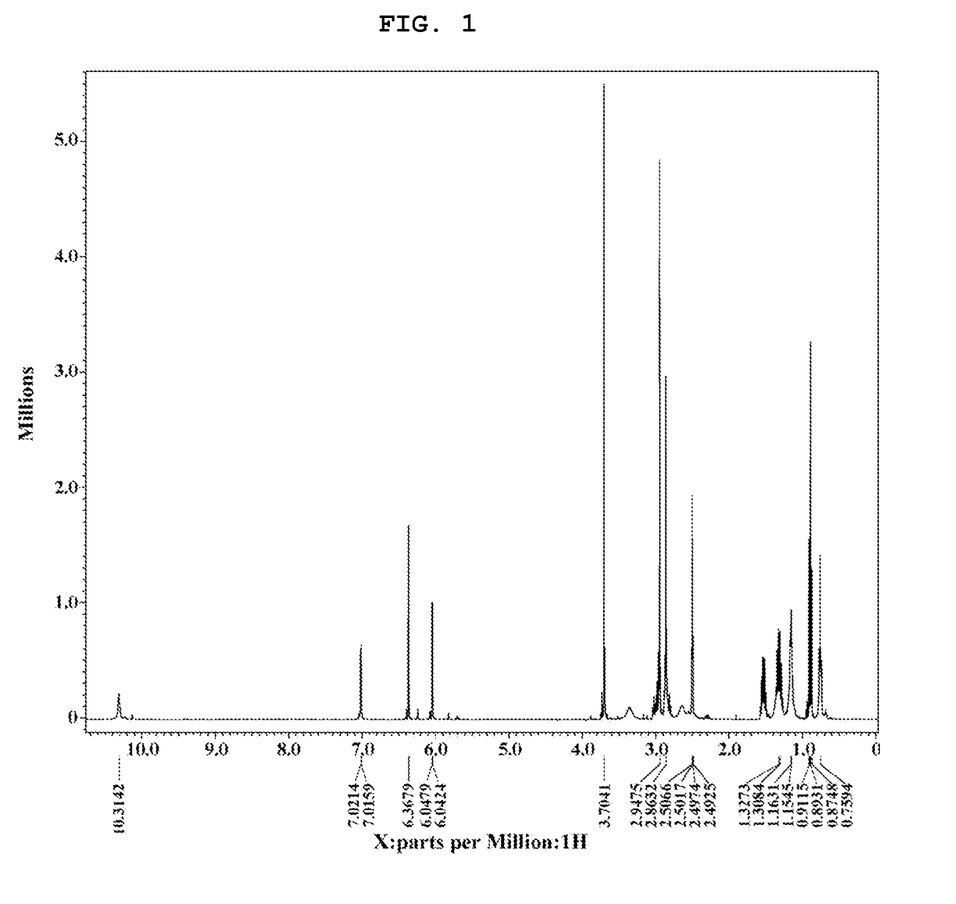
FIG. 1 is 1H NMR spectrum (400 MHz, DMSO-d6) of dimethyl lobamide according to an embodiment of the present invention.
Figure 2:
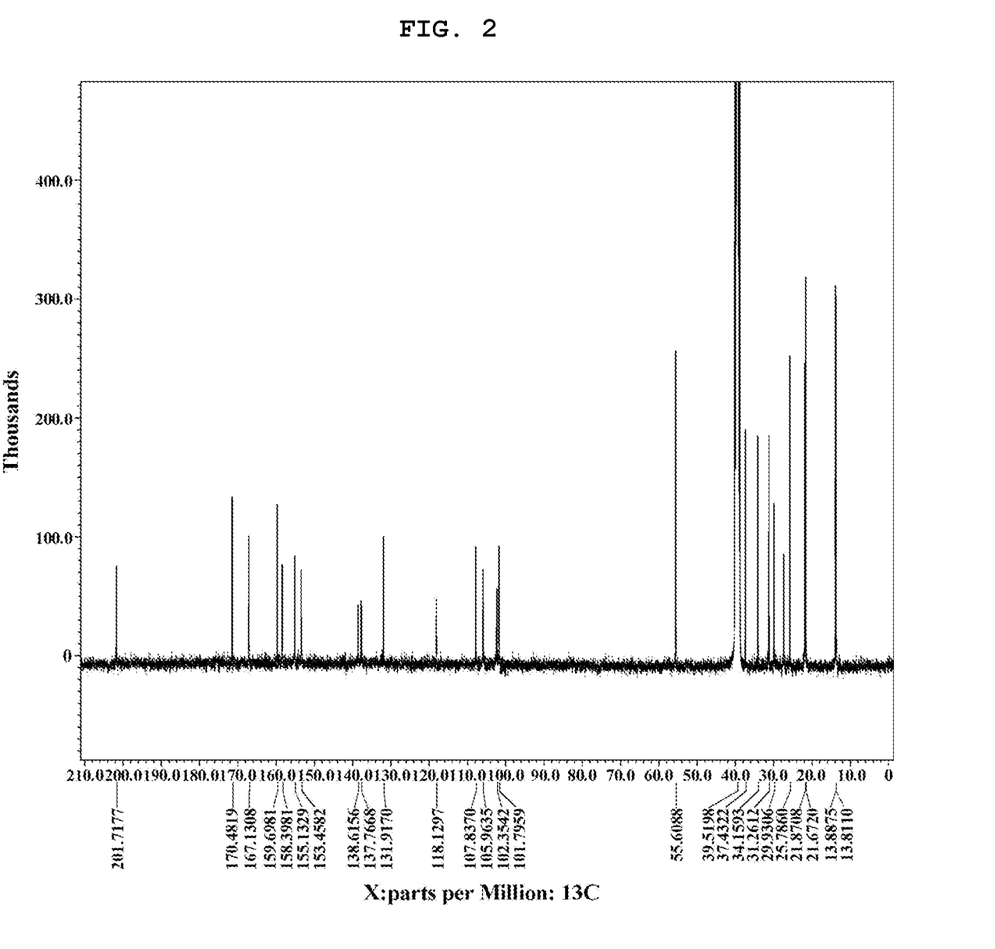
FIG. 2 is $^{13}$C NMR spectrum (100 MHz, DMSO-d6) of dimethyl lobamide according to an embodiment of the present invention.
Figure 3:
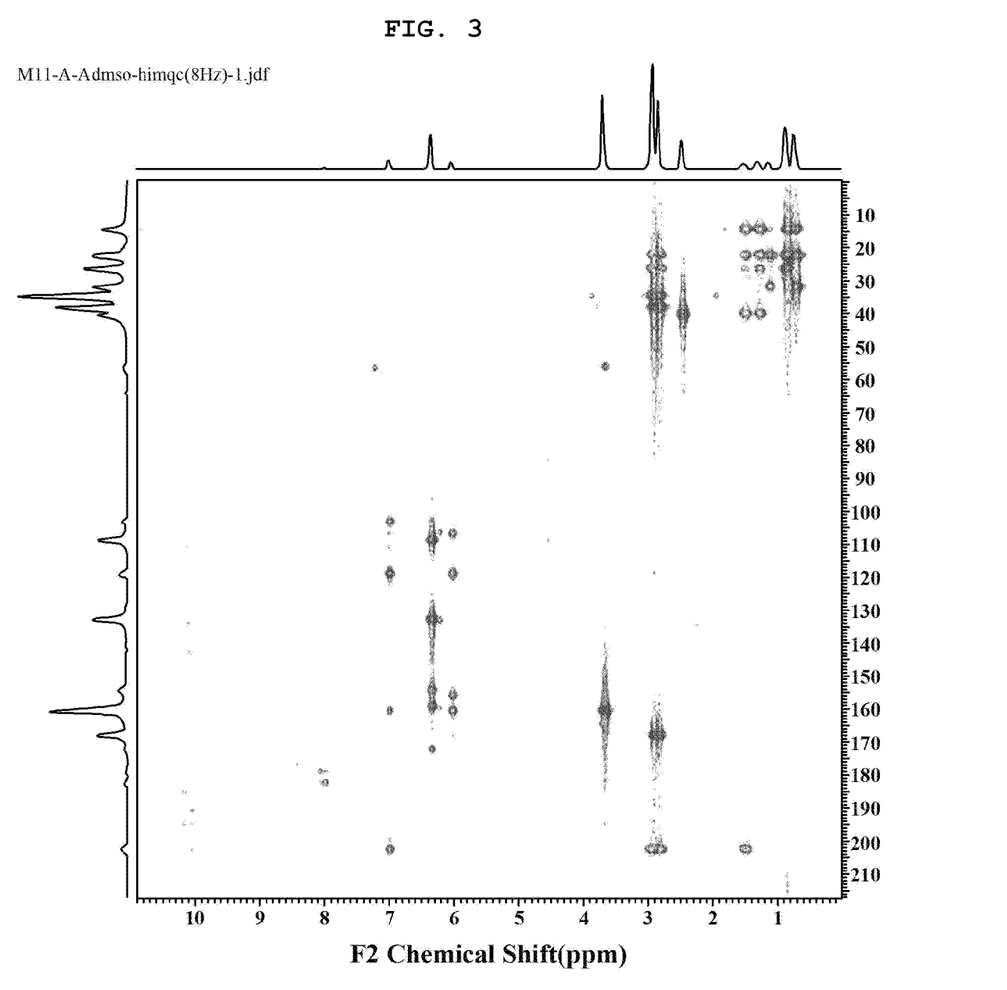
FIG. 3 illustrates HMQC data ($^1J_{CH}$=140 Hz, DMSO-d6) of dimethyl lobamide according to an embodiment of the present invention.
Figure 4:
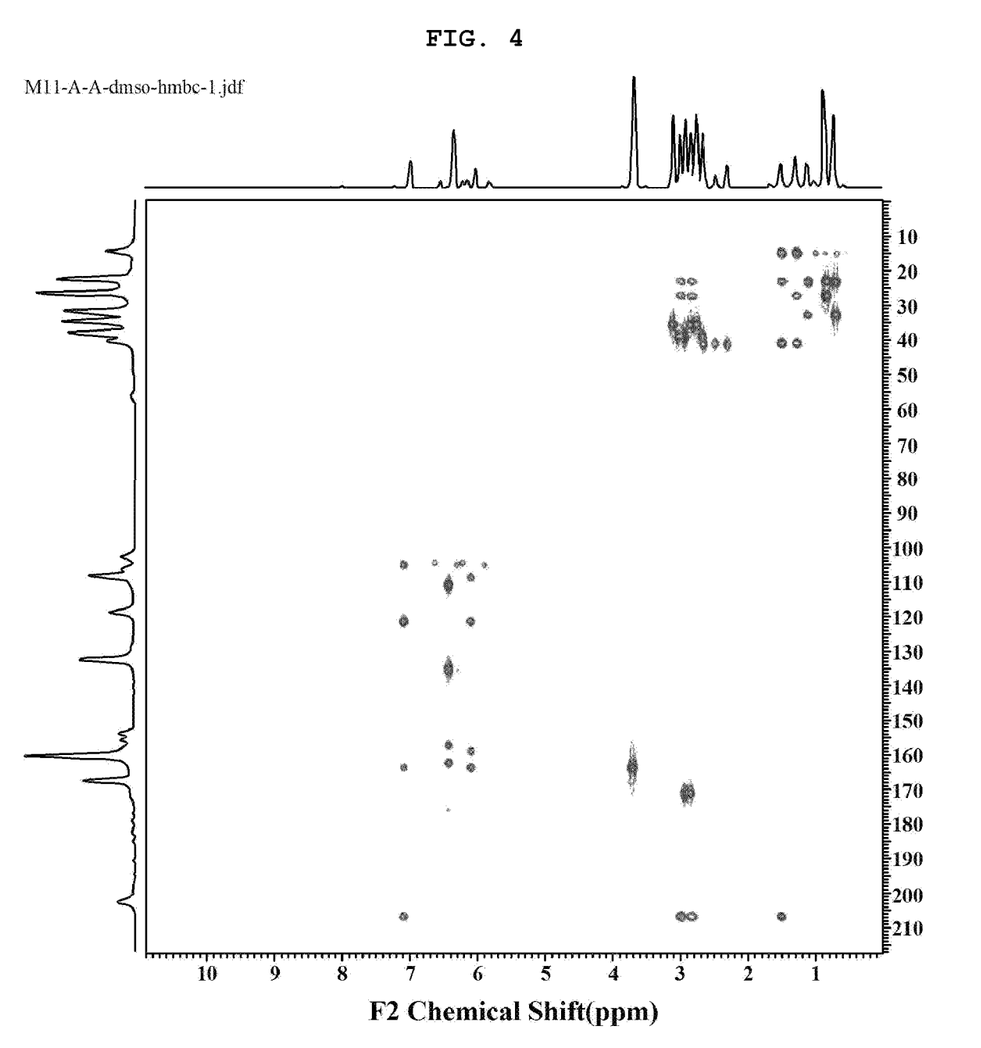
FIG. 4 illustrates HMBC data ($^nJ_{CH}$=8 Hz, DMSO-d6) of dimethyl lobamide according to an embodiment of the present invention.
Figure 5:
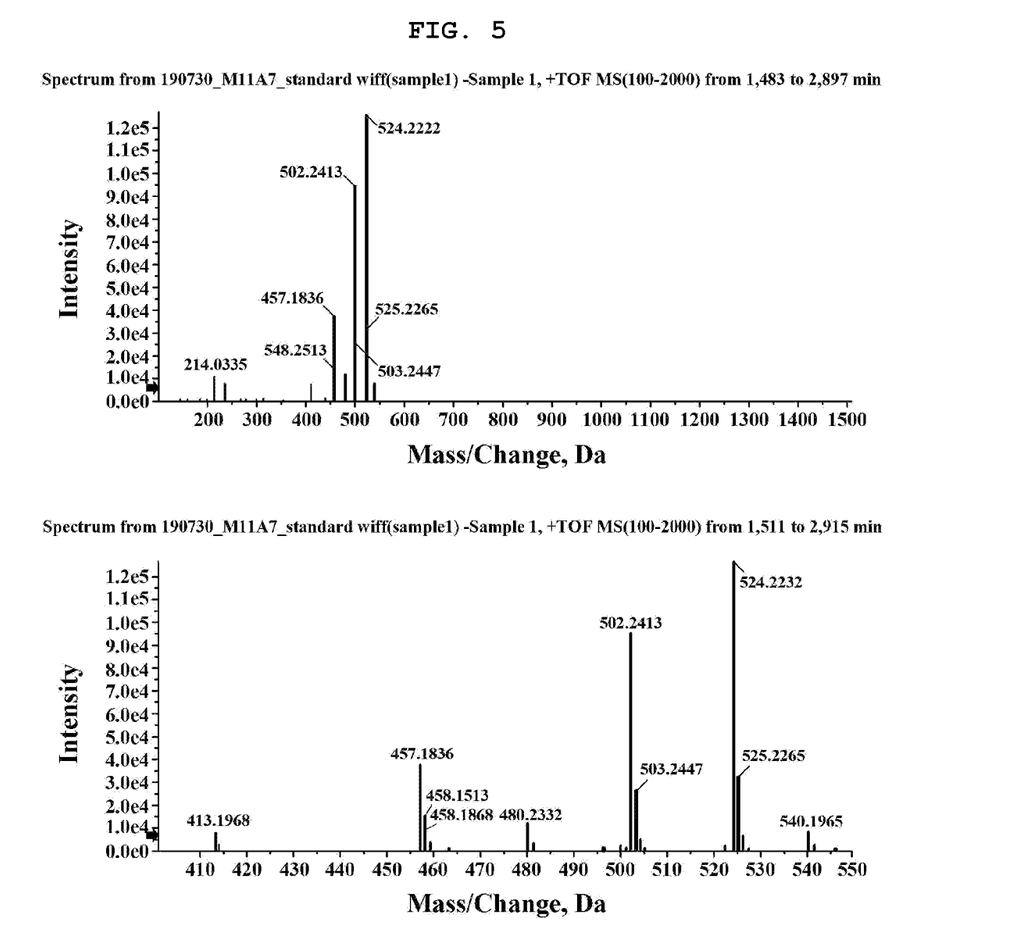
FIG. 5 illustrates HRESIMS data of dimethyl lobamide according to an embodiment of the present invention.
Figure 6:
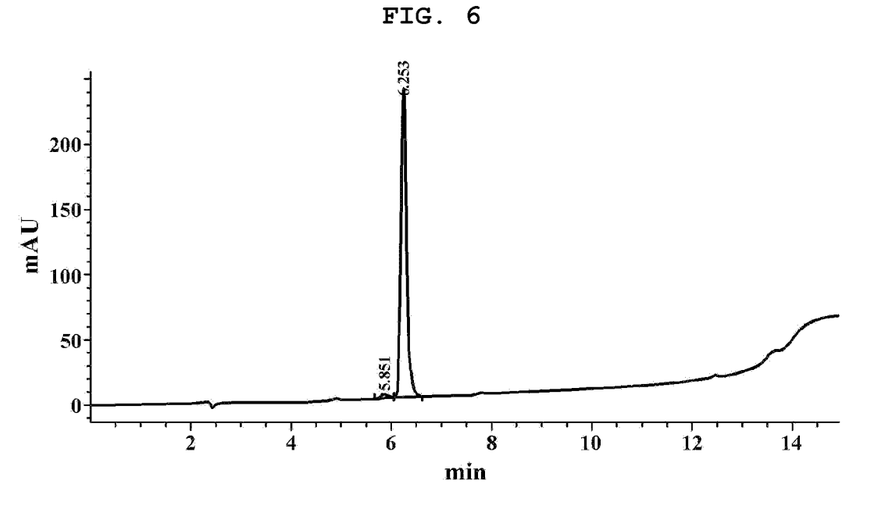
FIG. 6 illustrates HPLC (254 nm) data of dimethyl lobamide according to an embodiment of the present invention.

The structure of dimethyl lobamide was confirmed by analyzing NMR data of the synthesized material (FIG. 1). Each NMR data was measured using JOEL ECP-400 spectrometer (400 MHz for $^1$H and 100 MHz for $^{13}$C, JOEL, Japan) after dissolving the sample in DMSO-d6 solvent. A chemical shift value thereof was indicated with reference to the chemical shift value of DMSO-d6 (dC/dH=39.5/2.50 ppm), which was used as the solvent. Results thereof are shown in FIG. 2. In the case of 1H-detected heteronuclear multiple-quantum coherence (HMQC), this value was measured by setting $^1$J CH=140 Hz, and results thereof are shown in FIG. 3. Further, heteronuclear multiple-bond coherence (HMBC) measurement was performed after setting $^1$J CH=8 Hz, and results thereof are shown in FIG. 4. In addition, HRESIMS data of dimethyl lobamide is shown in FIG. 5, and HPLC (254 nm) data is shown in FIG. 6.

NMR data of dimethyl lobamide are shown in Table 1.

[Formula 2]

TABLE 1

NMR data of dimethyl lobamide

| Position | $\delta_C{}^a$, type | $\delta_H$, mult. (J in Hz)$^b$ |
|---|---|---|
| 1 | 118.1, C | |
| 2 | 155.1, C | |
| 3 | 102.4, CH | 6.04, d, 2.2 |
| 4 | 159.7, C | |
| 5 | 106.0, CH | 7.02, d, 2.2 |
| 6 | 138.6, C$^c$ | |
| 7 | 167.1, C | |
| 8 | 201.7, C | |
| 9 | 39.5, CH$_2$ | 2.99, m |
|  |  | 2.82, m |
| 10 | 25.8, CH$_2$ | 1.54, m |
| 11 | 21.7, CH$_2$ | 1.32, m |
| 12 | 13.9, CH$_3{}^d$ | 0.89, t, 7.3 |
| 1' | 107.8, C | |
| 2' | 158.4, C | |
| 3' | 101.8, CH | 6.37, s |
| 4' | 131.9, C | |
| 5' | 153.5, C | |
| 6' | 137.8, C | |
| 7' | 171.5, C | |
| 8' | 27.4, CH$_2$ | 2.64, m |
| 9' | 29.9, CH$_2$ | 1.34, m |
| 10' | 31.3, CH$_2$ | 1.16, m |
| 11' | 21.9, CH$_2$ | 1.16, m |
| 12' | 13.8, CH$_3{}^d$ | 0.76, t, 6.6 |
| N—CH3 | 37.4, CH$_3$ | 2.86, s |
| N—CH3 | 34.2, CH$_3$ | 2.95, s |
| 4-O—CH3 | 55.6, CH$_3$ | 3.70, s |
| 4'-OH |  | 10.31, s |

$^a$100 MHz,
$^b$400 MHz,
$^{c, d}$interchangeable

Example 3: Analysis of PTP-1B Inhibitory Activity of Dimethyl Lobamide

In order to analyze protein tyrosine phosphatase-1B (PTP-1B) inhibitory activity, enzyme activity was measured spectroscopically.

Specifically, to 0.5 μg/mL of PTP-1B (Bioneer, Korea), PTP-1B buffer (50 mM Bis-tris buffer, pH 6.5, 1 mM EDTA, 1 mM DTT), dimethyl lobamide (M11A7) (0, 0.4, 0.8, 1.6, 3.12, 6.25, 12.5, 25 nM) and the substrate pNPP (para Nitrophenyl phosphate, Sigma, USA) were added and reacted at room temperature for 30 minutes. Then, 10 N NaOH was added thereto, followed by reaction at room temperature for 5 minutes to terminate the reaction between PTP-1B, dimethyl lobamide and the substrate. Thereafter, the absorbance was measured at 405 nm.

Figure 7:
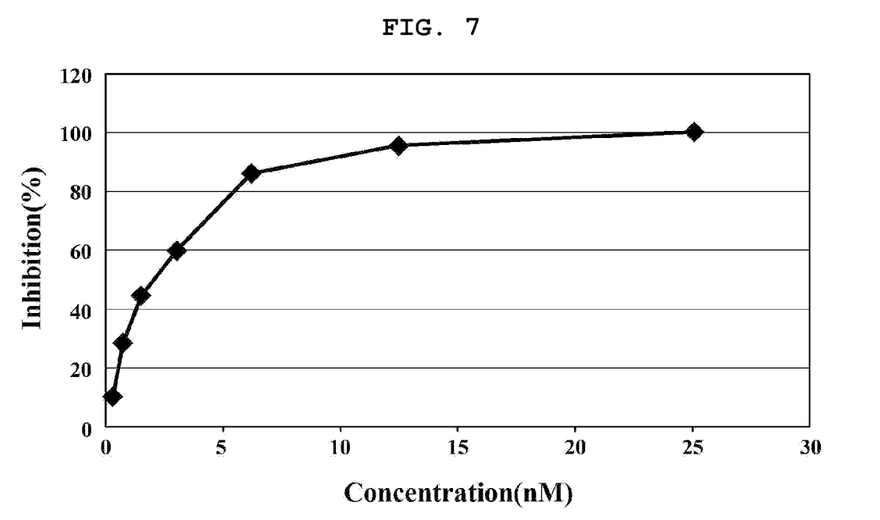
FIG. 7 is a graph illustrating PTP-1B inhibitory activity of dimethyl lobamide according to an embodiment of the present invention.

As shown in FIG. 7, as a result of analyzing the inhibitory activity of dimethyl lobamide (M11A7) on PTP-1B, IC$_{50}$ of lobarstin was 154 nM (Korean Patent Registration No. 10-1481141), while IC$_{50}$ of dimethyl lobamide was 2.16 nM, thereby exhibiting superior PTP-1B inhibitory effects than lobarstin. Further, it was confirmed that the inhibition rate was increased in a concentration-dependent manner.

Example 4: In-Vitro Antidiabetic Efficacy Test of Dimethyl Lobamide

To evaluate antidiabetic efficacy of dimethyl lobamide at in vitro level, expression changes of proteins involved in the glucose uptake mechanism of HepG2 (liver cancer cells) when treated with dimethyl lobamide were assayed.

To culture HepG2 cells, HepG2 cells were incubated in an EMEM medium containing 10% fetal bovine serum (FBS) and 1% penicillin/streptomycin and then seeded on a 6-well plate at a concentration of 5×10' cells/well. After culturing in an incubator (37° C., 5% CO$_2$) for 24 hours for cell attachment and stabilization, the existing medium was removed and a new medium, that is, EMEM serum free medium (EMEM 1% penicillin/streptomycin) was put at a concentration of 2 mL/well. After processing the samples by concentration, the culturing was performed for 20 hours.

After the end of the treatment time, insulin (10 nM) was added to the remaining cells except for cell groups 1 and 3 (Nos. 2, 3, 4, 5, 6 and 7) and the reaction was performed for 10 minutes.

Figure 8:
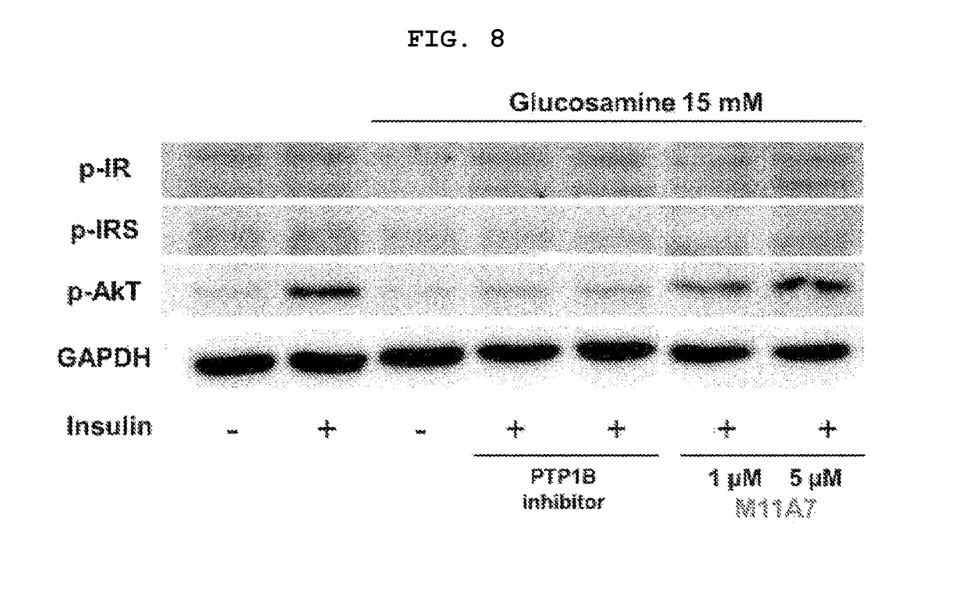
FIG. 8 illustrates in vitro test results of inhibitory activity of dimethyl lobamide according to an embodiment of the present invention.

The medium was entirely removed and 200 μl/well of lysis buffer (RIPA buffer containing 100× Proteinase inhibitor and 1× Phosphatase inhibitor) was added to gain the cell lysate. Then, after scraping off the cells stuck on the bottom using a scraper, the lysate was transferred to a tube and stored on ice for 20 minutes, followed by centrifugation (12500 g, 10 min, 4° C.). Only the supernatant was obtained and subjected to a BCA protein assay to check a protein concentration of each cell extract. Then, 5× protein dye was diluted to 1× according to the concentration and was boiled at 100° C. for 5 minutes. After performing SDS-PAGE with the prepared sample, the proteins in the gel were transferred to a PVDF membrane to prepare the next experiment. After blocking with PBST containing 5% skim milk for 30 minutes, the product was treated with the primary antibody and the secondary antibody sequentially. At this time, each of the antibodies was diluted with 5% skim milk base, and a dilution ratio was 1:1000 and 1:2000, respectively. Antibody treatment time was 12 hours and 1 hour, respectively. Further, immediately after treatment, the product was washed 3 times for 5 minutes with PBST. After processing the ECL solution for 1 minute, the band was detected by a membrane luminescence detector (ChemiDoc) (FIG. 8). In hepatocytes in which insulin resistance was not induced, after insulin treatment, a degree of tyrosine phosphorylation of each of insulin receptor and insulin substrate, which are proteins involved in the insulin delivery process, as well as a degree of serine phosphorylation of Akt, were determined by Western blot. As a result, the degree of phosphorylation was increased as compared to cells not treated with insulin. Further, in cells in which glycogen synthetase synthesized by insulin stimulation is suppressed using glucosamine to induce insulin resistance, protein phosphorylation in relation to insulin transfer was not increased due to insulin. On the other hand, in cells treated with 1 nM and 5 uM of dimethyl lobamide (M11A7), which is a PTB-1B inhibitor, it was confirmed that the degrees of tyrosine phosphorylation of the insulin receptor and the insulin substrate and the degree of serine phosphorylation of Akt were significantly increased.

Example 5: Verification of Efficacy of Dimethyl Lobamide in Diabetic Disease Model Animals Example 5-1: Observation of Changes in Blood Glucose after Oral Administration of Dimethyl Lobamide To more accurately measure antidiabetic effects of dimethyl lobamide, 200 μl of PBS as a control and 50 mg/kg of dimethyl lobamide compound as an experimental group were orally administered daily to 7-week-old male db/db mice (type 2 diabetes model animal, C57/BLKS/J-db/db, Korea Research Institute of Bioscience and Biotechnology). Thereafter, blood glucose was measured once a week. At this time, after oral administration, blood glucose was measured after fasting for 6 hours.

Figure 9:
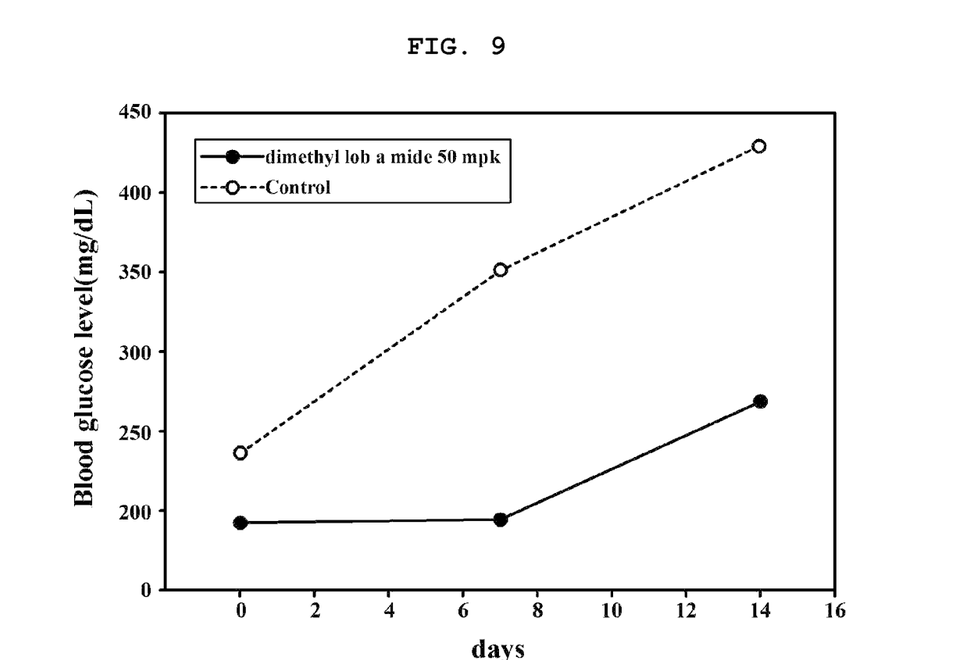
FIG. 9 is a graph illustrating blood glucose measurement results after fasting for 6 hours following oral administration of dimethyl lobamide according to an embodiment of the present invention for 2 weeks.

As a result, as shown in FIG. 9, the control (n=4) showed a rapid increase in blood sugar such as average of 238 mg/dL on day 0, 350 mg/dL on day 7, and 428 mg/dL on day 14, respectively. However, in the experimental group (n=4), to which 50 mg/kg of dimethyl lobamide was orally administered, a lower increase in blood glucose than the control, such as average of 193 mg/dL on day 0, 194 mg/dL on day 7, and 268 mg/dL on day 14, respectively, was measured.

This demonstrates antidiabetic effects similar to that of lobarstin, the fundamental substance. Specifically, although lobarstin had no antidiabetic effects by oral administration because it was not possible to be orally administered in diabetic disease model animals, dimethyl lobamide could have the antidiabetic effects by oral administration, and therefore, it was confirmed that development of a drug for oral administration using dimethyl lobamide is possible.

Example 5-2: Observation of Changes in Body Weight after Oral Administration of Dimethyl Lobamide To 7-week-old male db/db mice (type 2 diabetes model animal, C57/BLKS/J-db/db, Korea Research Institute of Bioscience and Biotechnology), 200 μl of PBS as a control and 50 mg/kg of dimethyl lobamide as an experimental group were orally administered daily. After administration, in order to investigate the change in body weight, the compound (dimethyl-lobamide) was orally administered twice a week at a fixed time, and then the body weight was measured using an animal scale.

As a result, the control (n=4) showed an average weight change of 32.05 g on day 0, 33.80 g on day 7, and 36.38 g on day 14, respectively, while the experimental group in which 50 mg/kg of compound (dimethyl-lobamide) was orally administered (n=4) showed an average weight change of 30.95 g on day 0, 31.78 g on day 7, and 34.86 g on day 14, respectively. This result indicates that there is no significant change in body weight in the type 2 diabetic animals treated with the compound (dimethyl-lobamide) compared to the control.

As such, the specific parts of the present invention have been described in detail above. Thus, it will be obvious to those skilled in the art that the specific descriptions are merely preferred embodiments, and the scope of the present invention is not limited thereto. Accordingly, it is intended that the substantial scope of the invention be defined by the claims and their equivalents.

What is claimed is:

1. A lobamide compound, or a salt thereof, represented by Formula 1

[Formula 1]

wherein $R_1$ is each independently H, a C1-C10 alkyl group or a C2-C10 allyl group;

$R_2$ is H, a C1-C10 alkyl group, a C2-C10 allyl group, an acyl group, a C1-C10 hydroxyalkyl group or a C1-C10 aminoalkyl group;

$R_7$ is an amide group;

$R_3$ is a carboxylic acid or an amide group;

$R_4$ is a C1-C10 alkoxy group or a hydroxyl group;

$R_6$ is a C1-C10 alkoxy group or a hydroxyl group; and $R_5$ is a C1-C10 alkoxy group or a hydroxyl group.

2. The lobamide compound according to claim 1, wherein the lobamide compound is dimethyl lobamide represented by Formula 2:

[Formula 2]

3. A method for preparation of a lobamide compound represented by Formula 1, the method comprising:
(a) reacting a compound having a depsidone structure represented by Formula 4 with an amine-based reagent:

[Formula 4]

wherein $R_1$ is each independently H, a C1-C10 alkyl group or a C2-C10 allyl group;
$R_2$ is H, a C1-C10 alkyl group, a C2-C10 allyl group, an acyl group, a C1-C10 hydroxyalkyl group or a C1-C10 aminoalkyl group;
$R_3$ is a carboxylic acid or an amide group;
$R_4$ is a C1-C10 alkoxy group or a hydroxyl group; and
$R_5$ is a C1-C10 alkoxy group or a hydroxyl group; and
(b) obtaining a compound in a form of an amide represented by Formula 1:

[Formula 1]

wherein $R_1$ is each independently H, a C1-C10 alkyl group or a C2-C10 allyl group;
$R_2$ is H, a C1-C10 alkyl group, a C2-C10 allyl group, an acyl group, a C1-C10 hydroxyalkyl group or a C1-C10 aminoalkyl group;
$R_7$ is an amide group;
$R_3$ is a carboxylic acid or an amide group;
$R_4$ is a C1-C10 alkoxy group or a hydroxyl group;
$R_6$ is a C1-C10 alkoxy group or a hydroxyl group; and
$R_5$ is a C1-C10 alkoxy group or a hydroxyl group.

4. A method for preparation of a dimethyl lobamide compound represented by Formula 2, the method comprising:
(a) reacting lobaric acid represented by Formula 3 with dimethylamine; and
(b) obtaining dimethyl lobamide represented by Formula 2:

[Formula 2]

[Formula 3]

5. The method according to claim 4, wherein the lobaric acid is extracted from *Stereocaulon alpinum*.

6. The method according to claim 4, further comprising:
obtaining crystals containing lobaric acid by recrystallizing the *Stereocaulon alpinum* extract before performing the (a),
wherein the (a) comprises:
dissolving the crystals in a solvent, adding dimethylamine thereto and stirring the mixture; and
after the stirring, adding an acidic solution thereto to terminate the reaction.

7. A method for treatment of diabetes, the method comprising administering to a subject in need thereof a composition comprising the lobamide compound according to claim 1 or a salt thereof as an active ingredient.

8. The method according to claim 7, wherein the lobamide compound is dimethyl lobamide represented by Formula 2:

[Formula 2]

9. The method according to claim 7, wherein the composition further comprises an antidiabetic compound.

10. The method according to claim 9, wherein the antidiabetic compound is any one selected from the group consisting of nateglinide, repaglinide, glitazones, sulfonyl urea, metformin, glimepride, thiazolidinedione, biguanide, acarbose as alpha-glucosidase inhibitor, and meglitinide-based frandins.

11. The method according to claim 7, wherein the composition is a health functional food.

12. The method according to claim 11, wherein the lobamide compound is dimethyl lobamide represented by Formula 2:

[Formula 2]

13. The method according to claim 7, wherein the composition is a pharmaceutical composition.

14. The method according to claim 3, wherein the compound having the depsidone structure is extracted from *Stereocaulon alpinum*.

15. The method according to claim 3, further comprising:
obtaining crystals containing compound having the depsidone structure by recrystallizing the *Stereocaulon alpinum* extract before performing the (a),
wherein the (a) comprises:
dissolving the crystals in a solvent, adding dimethylamine thereto and stirring the mixture; and
after the stirring, adding an acidic solution thereto to terminate the reaction.

* * * * *